(12) United States Patent
Crofford

(10) Patent No.: US 6,695,883 B2
(45) Date of Patent: Feb. 24, 2004

(54) FEMORAL NECK FIXATION PROSTHESIS

(76) Inventor: Theodore W. Crofford, 3741 Kelvin Ave., Fort Worth, TX (US) 76133

( * ) Notice: Subject to any disclaimer, the term of this patent is extended or adjusted under 35 U.S.C. 154(b) by 0 days.

(21) Appl. No.: 10/228,907

(22) Filed: Aug. 27, 2002

(65) Prior Publication Data

US 2003/0195635 A1 Oct. 16, 2003

Related U.S. Application Data

(60) Provisional application No. 60/371,837, filed on Apr. 11, 2002.

(51) Int. Cl.$^7$ ............................... A61F 2/30; A61F 2/36
(52) U.S. Cl. ................................................. 623/22.46
(58) Field of Search .......................... 623/23.11, 23.15, 623/23.21, 23.22, 23.26, 23.27, 22.15, 22.4, 22.43, 22.44, 22.46, 23.12, 23.14, 22.42

(56) References Cited

U.S. PATENT DOCUMENTS

| | | | |
|---|---|---|---|
| 4,129,903 A | 12/1978 | Huggler | |
| 4,224,699 A | 9/1980 | Weber | |
| 4,795,473 A | 1/1989 | Grimes | |
| 4,976,740 A | * 12/1990 | Kleiner | 623/23.14 |
| 5,035,717 A | 7/1991 | Brooks | |
| 5,133,760 A | 7/1992 | Petersen et al. | |
| 5,147,403 A | 9/1992 | Gitelis | |
| 5,318,571 A | 6/1994 | Benson | |
| 5,376,125 A | 12/1994 | Winkler | |
| 5,571,203 A | 11/1996 | Masini | |
| 5,741,262 A | 4/1998 | Albrektsson et al. | |
| 5,800,553 A | * 9/1998 | Albrektsson et al. | 623/22.4 |
| 5,980,575 A | 11/1999 | Albrektsson et al. | |
| 6,273,915 B1 | 8/2001 | Grimes | |
| 6,284,002 B1 | 9/2001 | Sotereanos | |
| 6,379,390 B1 | 4/2002 | Advani et al. | |
| 6,383,227 B1 | * 5/2002 | Baroud et al. | 623/23.22 |
| 2002/0045950 A1 | * 4/2002 | Draenert | 623/23.26 |
| 2002/0133234 A1 | 9/2002 | Sotereaneos | |

OTHER PUBLICATIONS

Harlan C. Amstutz, MD, and Peter Grigoris, MD. PhD, Metal on Metal Bearings in Hip Arthroplasty, Clinical Orthopaedics and Related Research, 1996, No. 329S, pp. S11–S34.

A.H.Huggler, M.D., and H.A.C. Jacob, Ph.D., (Eds.) The Thrust Plate Hip Prosthesis, Springer–Verlag Berlin Heidelberg 1997, 3 pages submitted.

Tomas Albrektsson, MD, PhD, et al. Gothenburg Osseointegrated Hip Arthroplasty: Experience With a Novel Type of Hip Design, Clinical Orthopaedics and Related Research, 1998, No. 352, pp. 81–94.

Prof. Dr. A.H. Huggler, and Dr. Ing.H.A.C. Jacob, The Thrust Plate Prosthesis, All Pro, Jan. 1993, 16 pages.

H. Bereiter, et al., The Thrust Plate Prosthesis (TPP) A New Concept in Hip Prothesis Design Eight Years of Clinical Experience, Orthop, Date Unknown, REL SCI 2, 11 pages.

A.H. Huggler and H.A.C. Jacob, The Uncemented Thrust–Plate Hip Prosthesis, Date Unknown, 5 pages.

* cited by examiner

Primary Examiner—Pedro Philogene
Assistant Examiner—David A Bonderer
(74) Attorney, Agent, or Firm—Thompson & Knight LLP; Robert C. Hilton

(57) ABSTRACT

A femoral neck fixation prosthesis and method of using same which reduces bone loss and the avoids the other shortcomings of the prior art by allowing the fixation of a stable femoral head replacement while reducing the amount of the femur which must be reamed for the insertion of the prosthesis. The preferred embodiment provides that the femoral head is attached to a fixation prosthesis which extends coaxially through the canal of the femoral neck, into the femur, and is then attached to the opposite lateral wall of the femur. In this manner, the prosthesis serves to imitate the original structure of the femoral neck. No other support members, either crosspins or arms extending into the length of the femur, are required.

19 Claims, 7 Drawing Sheets

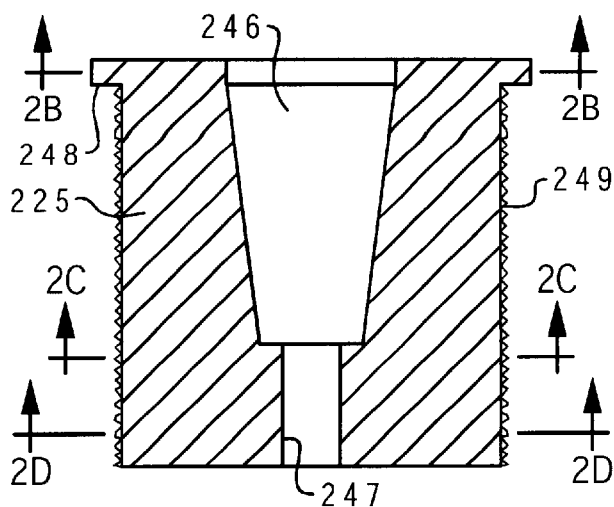
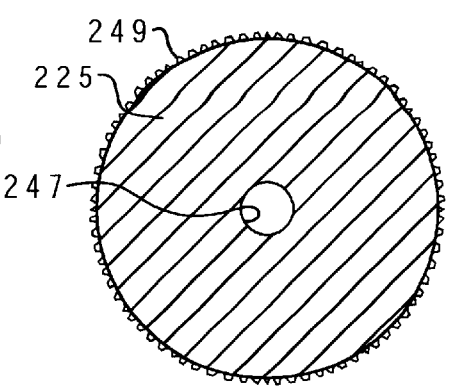
*Fig. 2C*
*Fig. 2A*
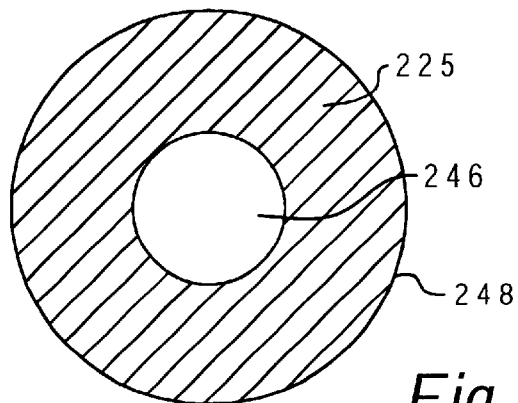
*Fig. 2B*
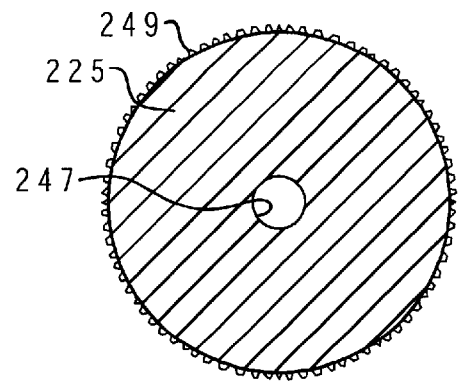
*Fig. 2D*
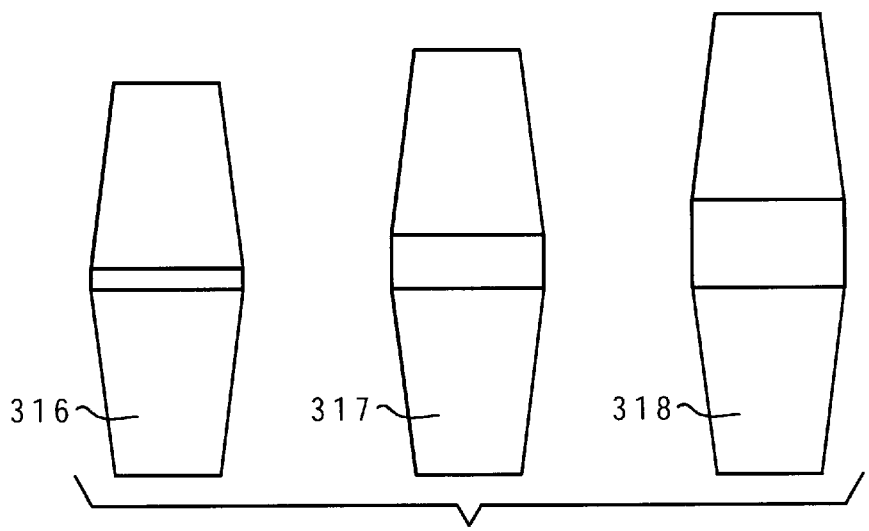
*Fig. 3*

FEMORAL NECK FIXATION PROSTHESIS

CROSS-REFERENCE TO OTHER APPLICATION

This application claims priority from U.S. Provisional Application No. 60/371,837, filed Apr. 11, 2002 (MM/DD/YYYY), which is hereby incorporated by reference.

TECHNICAL FIELD

The present application relates to an improved apparatus and method for hip replacements, and more specifically to a less-invasive prosthetic which replaces the femoral head while retaining the natural femoral neck.

DESCRIPTION OF THE RELATED ART

A widely used design for replacement of the proximal portion of a femur employs an elongate, often curved, shaft that extends into the medullary canal of the femur. This design has the tendency to place unnatural stresses on the femur which lead to pain and the consequent curtailment of activity for the patient. Further, present techniques can lead to proximal bone loss and call for the resection of the majority of the femoral neck. Current designs also call for fixing the prosthesis in the proximal third of the femur. The useful life of an intramedullary implant is often less than the expected life span of a young patient.

Previously known prostheses for replacing a femoral head that do not extend into the medullary canal have been mechanically complex or have proven troublesome in actual use. Huggler, U.S. Pat. No. 4,129,903 and Grimes, U.S. Pat. No. 4,795,473 are examples of prosthetic implants having a side plate attached to the exterior lateral side of the femur opposite the femoral head. Screws are used to secure the plate to the femur and one or more holes are drilled into the femur for securing the plate to the bone. The additional holes and the stresses at the site of fixation are believed to cause trauma to the bone.

Masini, U.S. Pat. No. 5,571,203 discloses a device having a shaft that extends through a resected portion of the proximal femur, positioned co-axially relative to the longitudinal axis of the femur. The device is secured by a screw or similar locking device that extends into the femur from the lateral side, just below the greater trochanter. It is believed that the natural forces applied to the prosthesis during normal hip motion result in the application of shear forces to the greater trochanter. The shear forces can be harmful to the greater trochanter and can permit micro-movement of the prosthesis on the unsecured side.

A conventional method for implanting the above types of femoral head implants is described in Campbell's Operative Orthopaedics, (Mosby, 7th ed., 1987) and typically includes making a large incision in the patient's lateral side at the hip joint and through the skin and muscle, dislocating the hip and then sawing off the femoral head. This method is considered invasive because of the need to dislocate the hip and cut through muscle surrounding the hip joint. Invasive procedures increase the trauma to the patient, the potential for complications, recovery time and the cost.

Replacement of the proximal portion of the femur is sometimes necessary due to degenerative bone disorders or trauma to otherwise healthy bone caused by accidental injury. In the latter instance it is desirable to replace the traumatized portion of the bone without causing further trauma to healthy bone. There is a need, therefore, for an implant that replaces a traumatized portion of the femur, but also significantly minimizes stress to the remaining healthy bone and that can be implanted by a method that is less invasive.

There are several other significant remaining problems and issues relating to hip arthroplasty. They include:

The Young, Active Patient:
Younger patients are more likely to have failure of their primary arthroplasty both due to increased demand on the mechanical construct, and from a pure life expectancy standpoint. It follows that they are more likely to require a revision and a second revision, which may lead to a catastrophic bone loss situation.

Instability:
This problem still occurs at the same rate that it did 50 years ago. Larger femoral heads may decrease the incidence, but no other significant technical changes have occurred to effect the incidence of this serious complication.

Bone Loss:
The overwhelming majority of present successful femoral prosthesis achieves fixation at least as far distal as the proximal femoral metaphysis. When these prosthesis fail, the next step usually involves diaphyseal fixation, often with a large diameter stiff stem.

Leg Length Inequality:
Leg length inequality after hip arthroplasty has always been a problem and an average lengthening of the leg of 1 centimeter is common. Lengthening is sometimes accepted for the sake of improved stability. Leg length inequality has been reported as the number one reason why surgeons are sued after hip arthroplasty Surgical Morbidity:
Hip arthroplasty usually involves significant blood loss, body fluid alterations and pain. Shortly, it's a big operation that hurts. It should be the goal of every compassionate surgeon to minimize these issues. If the operation can be made smaller, with less blood loss and less pain without diminishing long term results, every effort should be made to do so.

It would therefore be desirable to provide a femoral next prosthetic apparatus that overcomes these significant disadvantages.

SUMMARY OF THE INVENTION

It is therefore one object of the present invention to provide an improved apparatus and method for hip replacements.

It is another object of the present invention to provide an improved and less-invasive prosthetic which replaces the femoral head while retaining a substantially intact femoral neck.

The foregoing objects are achieved as is now described. The preferred embodiment provides a femoral neck fixation prosthesis and method of using same which reduces bone loss and avoids the other shortcomings of the prior art by allowing the fixation of a stable femoral head replacement while reducing the amount of the femur which must be reamed for the insertion of the prosthesis. The preferred embodiment provides that the femoral head is attached to a fixation prosthesis which extends coaxially through the central canal of the femoral neck, into the femur, and is then attached to the opposite lateral wall of the femur. In this manner, the prosthesis serves to imitate the original structure of the femoral neck. No other support members, either crosspins or arms extending into the length of the femur, are required.

The above as well as additional objectives, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of illustrative sample embodiments when read in conjunction with the accompanying drawings, wherein:

FIG. 3 depicts a schematic of the femoral necks of a prosthesis in accordance with a preferred embodiment of the present invention;

DETAILED DESCRIPTION OF THE PREFERRED EMBODIMENTS

Figure 1:
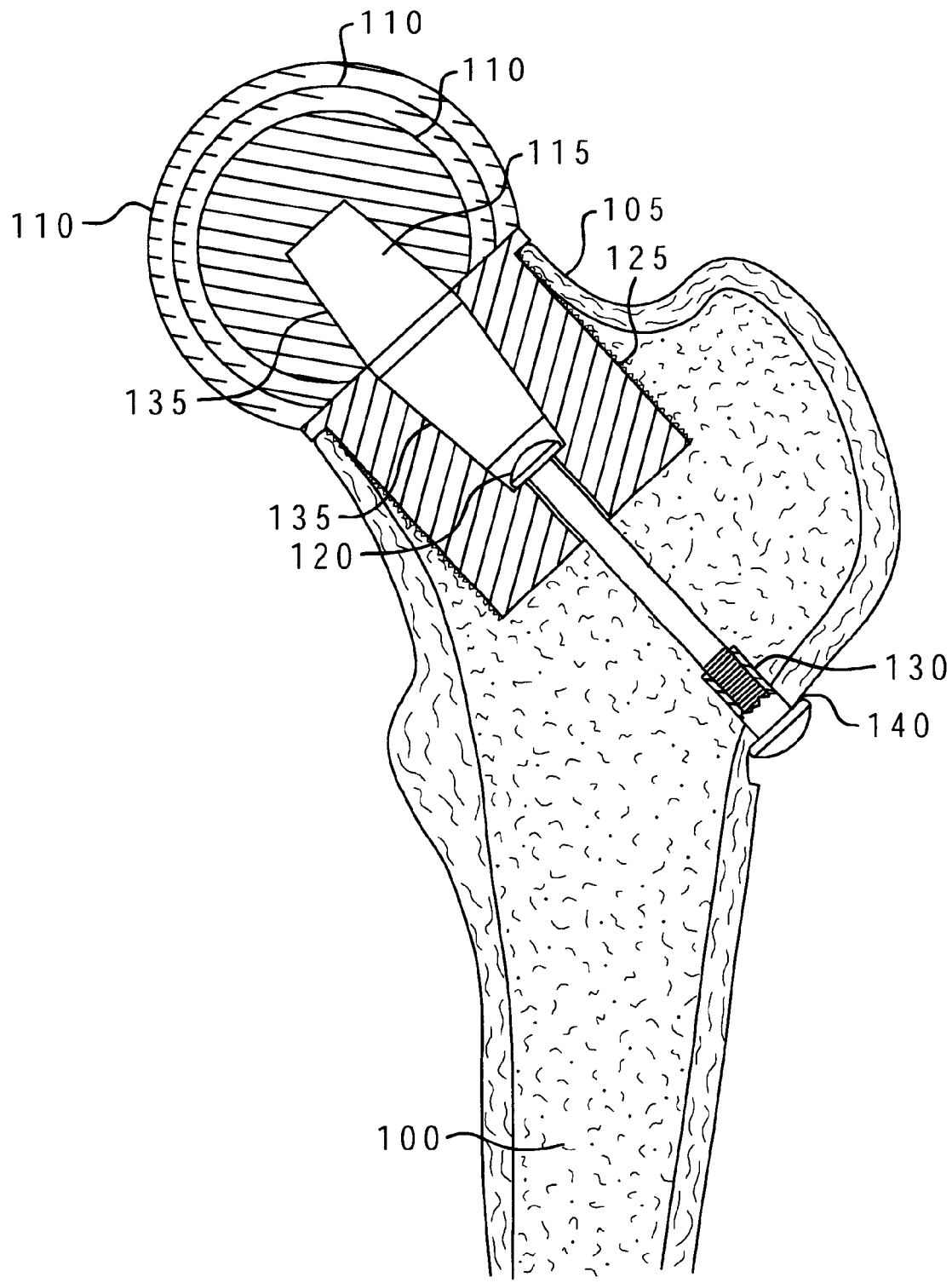
FIG. 1 depicts a schematic of an anterior view of a prosthesis in accordance with a preferred embodiment of the present invention.

The numerous innovative teachings of the present application will be described with particular reference to the presently preferred embodiment (by way of example, and not of limitation).

The preferred embodiment provides a femoral neck fixation prosthesis and method of using same which reduces bone loss and the avoids the other shortcomings of the prior art by allowing the fixation of a stable femoral head replacement while reducing the amount of the femur which must be removed and reamed for the insertion of the prosthesis. The preferred embodiment provides that the femoral head is attached to a fixation prosthesis which extends coaxially through the central canal of the femoral neck, into the femur, and is then attached to the opposite lateral wall of the femur. In this manner, the prosthesis serves to imitate the original structure of the femoral head while substantially retaining the natural femoral neck. No other support members, either crosspins or arms extending into the length of the femur, are required.

A femoral neck fixation prosthesis in accordance with the preferred embodiments is designed to achieve fixation in the isthmus of the femoral neck with or without cement. Therefore, revision of the disclosed femoral neck fixation prosthesis would essentially become the complexity of a present day primary hip arthroplasty for the femoral component. The improved femoral neck fixation prosthesis would require an operation equivalent to a primary arthroplasty on the femoral side. Therefore it would be ideal for the younger patient, but would also be recommended for the older patients with accommodating anatomy.

The innovative method for implanting the femoral neck fixation prosthesis would allow less muscular dissection, and the capsule can be repaired anteriorly at the end of the procedure. The disclosed femoral neck fixation prosthesis is designed to be used with larger diameter femoral heads. The combination of these factors would significantly improve stability of the hip. The goal is to minimize the need for hip position precautions postoperatively.

One advantage of the preferred embodiment is that less bone would be resected initially using the femoral neck fixation prosthesis, and the stress would be transferred to the bone in the femoral neck. The metaphysis and the diaphysis of the proximal femur would be minimally disturbed. Only the femoral head itself will be resected.

Another advantage of the preferred embodiment, is that the femoral neck length and offset would be accurately measured and reproduced when using the femoral neck fixation prosthesis. Leg length inequality due to hip arthroplasty could be minimized and muscle mechanics could be accurately restored.

Further, an operation using the femoral neck fixation prosthesis would be less invasive with less blood loss, less post operative pain, and less perioperative morbidity than the an operation that employs the vast majority of commonly used prosthesis. The economic implications of a shorter hospital stay, fewer blood transfusions, and fewer medical complications are significant.

The preferred embodiment of the present invention is shown in FIG. 1, wherein femur 100 is shown with femoral neck 105, joining member 115, and prosthetic head 110.

The preferred embodiment provides an uncemented porous coated femoral prosthesis body 125 with a modular head 110 and joining member 115. The metal used is preferably either titanium or chrome-cobalt based, and can be any metal commonly used in hip prosthesis construction. The modulus of elasticity of such a short segment will be of less significance than in a standard femoral stem. The coating is preferably either sintered beads or plasma sprayed, depending on the type of metal used for the body of the prosthesis.

The body 125 of the prosthesis will preferably be available in various diameters, approximately every 1–1.5 mm. The length of the prosthesis will preferably be chosen from one or two lengths, approximately 30 mm. Most of the fixation and ingrowth of the bone to the prosthesis will occur in the first 10–20 mm.

Fixation to the femur will be achieved by reaming the femoral neck 105 to accommodate a cylindrical porous coated sleeve body 125, which is supported by a proximal collar and given distal stability with a compression screw 120 through the lateral wall of the femur just distal to the greater tuberosity (location 140). Reaming will be progressive until the cortex of the femoral neck is encountered. A femoral component ½ mm greater than the last diameter reamed will then be selected.

After insertion, the long axis of the body of the component body 125 will coincide with the axis made in the preoperative femur 100 by an imaginary line connecting the center of the femoral neck 105 with the center of the femoral head 110. Resection of the femoral head will be measured such that the center of rotation of the femoral head 110 can be measured and reproduced. The femoral neck 105 will be reamed with a flat reamer that fits in the reamed canal of the femoral neck 105 to establish a flat surface. The proximal body 125 of the prosthesis will have the female end of a morse taper to allow the attachment of the joining member 115.

A compression screw 120 passes through the center of the body of the prosthesis. This screw attaches to a barrel nut 130 in the lateral wall of the femur at point 140 and preferably has a hexagonal head. The screw 120 is preferably smooth in the segment within the body of the prosthesis and has threads on the distal end. The tunnel through the body of the prosthesis forms a snug fit around the smooth portion of the screw 120. The barrel nut 130 is preferably angled to be flush with the lateral side of the femur at point 140. The head of the screw 120 is preferably located in the base of the morse taper in the body 125 of the femoral component. This screw 120 adds stability to the construct by giving antero-posterior and varus-valgus stability to the body 125 of the prosthesis and by compressing the prosthesis on the neck 105 of the femur 100. These screws will be available in various lengths.

It is important to note that this innovative design allows the prosthesis to be installed and used without requiring any other fastener on the femur. In particular, the preferred embodiment does not require any additional screws or other fasteners to be placed in the femur, and does not require any sort of support plate on the lateral wall of the femur.

Male-male morse taper joining member 115 acts as a joining portion in connecting the body 125 of the prosthesis to the femoral head 110. Adjustments in joining member length will occur in this segment with several lengths of joining member segments available for each femoral body and femoral head. The joining member segment needed to exactly reproduce the center of rotation of the femoral head will be known based on the amount of bone resected. In this embodiment, the joining member 115 has male morse tapers 135 on each side, and will have a variable-length section in between the morse tapers to fit the specific patient.

The femoral head 110 will have a female morse taper to connect to the joining member 115. Femoral heads 110 will be of various diameters depending on the acetabulum, and several exemplary sizes are shown in FIG. 1. Ideally larger femoral head diameters (e.g., 36 mm to 50 mm) are used to both improve stability and prevent impingement of the neck on the acetabular rim. The femoral head 110 is preferably polished chrome-cobalt, as the industry standard, but other materials can be used.

In another embodiment of the present invention, a de-rotation component is added to reduce the likelihood of the rotation of the prosthesis within the femoral neck. This can be accomplished with a pin or stem with grooves or slots that passes through the lateral cortex into the body of the prosthesis. This would then be compressed with a screw which would be put through the head end of the body of the prosthesis into the stem.

It should be clear that the prosthesis of the preferred embodiments can be used with or without a cement.

FIGS. 2A–2C shows several cross-section views of the cylindrical porous coated body 225 of the prosthesis of the preferred embodiment. FIG. 2A shows a longitudinal cross-section of the body 225. In this view, a collar 248 at the proximal end of the body 225 is illustrated, as is the female morse taper cavity 246 which is fit to receive the joining member. The collar 248 is configured to abut the proximal end of the resected femoral neck. Communicating with cavity 246 is tubular channel 247 which will receive the compression screw. Below the collar 248, the exterior of the body 225 has a porous coated layer 249.

Figure 2E:
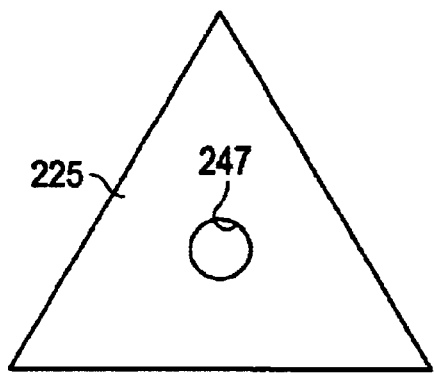
FIG. 2 shows a schematic of the cross section at various levels of the body of a prosthesis in accordance with a preferred embodiment of the present invention.
Figure 2F:
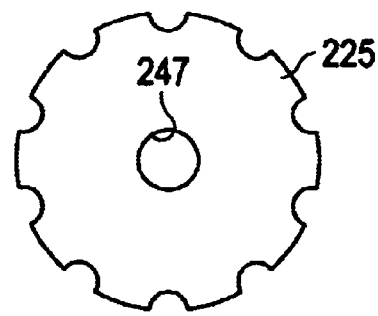
Figure 2G:
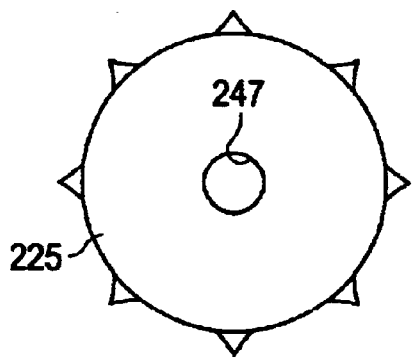
Figure 2H:
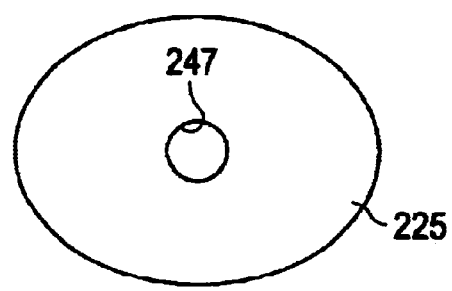

While the preferred embodiment has a substantially circular cross-section, as shown in FIGS. 2A–2C, the body member 225 can also be configured with a triangular (FIG. 2E), scalloped (FIG. 2F), oval (FIG. 2H), or fluted (FIG. 2G) cross-section.

FIG. 2B shows a lateral cross-section of body 225 as cut across line B of FIG. 2A. In FIG. 2B, the cavity 246 is shown, and the proximal collar 248 is also illustrated.

FIG. 2C shows a lateral cross-section of body 225 as cut across line C of FIG. 2A. In FIG. 2C, channel 247 for the compression screw is shown passing through the center of body 225. On the exterior of body 225 is shown the porous coated layer 249. A cross-section across line D of FIG. 2A is the same as described for line C of that figure.

FIG. 3 shows joining members 316/317/318 of various sizes, which can be used for patients with differing requirements. Each joining member 316/317/318 has a morse taper on each end, and a variable-length straight section connecting the morse tapers.

Figure 4:
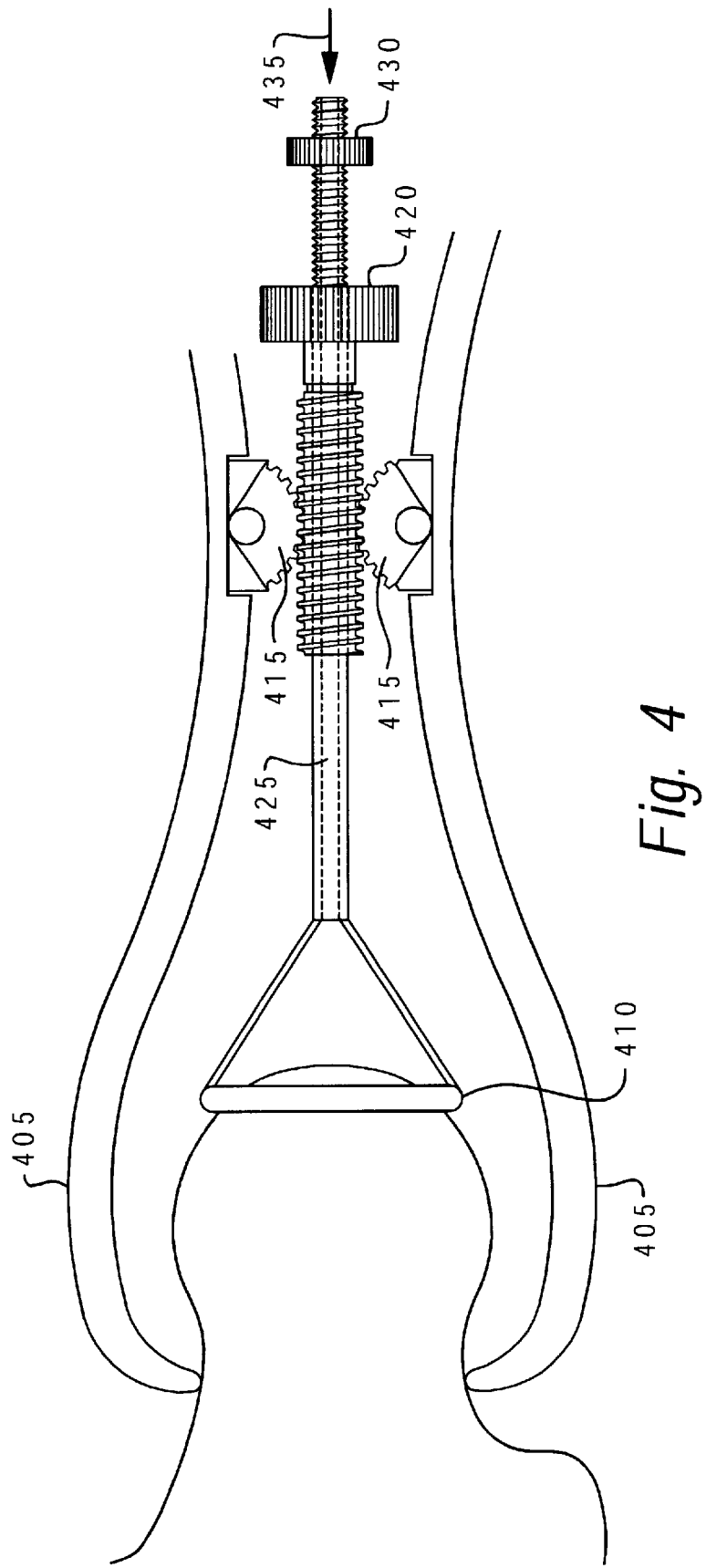
FIG. 4 depicts the centering guide for placement of the starting pin in accordance with a preferred embodiment of the present invention.

FIG. 4 depicts the centering guide for placement of the starting pin in accordance with a preferred embodiment of the present invention. In this figure, femoral neck gripping clamp 405 is to grip and hold the femoral neck after the femoral head centering device 410 has been placed over the patient's femoral head.

The femoral neck gripping clamp 405 is expanded or contracted using adjustment piece 420, which operates gears 415. Cannulated rod 425, which is connected to femoral head centering device 410, allows pin insertion into the cannula at 435.

Free nut 430 is used to tighten the femoral head centering device 410. The centering guide shown in FIG. 4 is preferably made of a stiff metal, and can also be used as a retractor to expose the femoral head.

Figure 5:
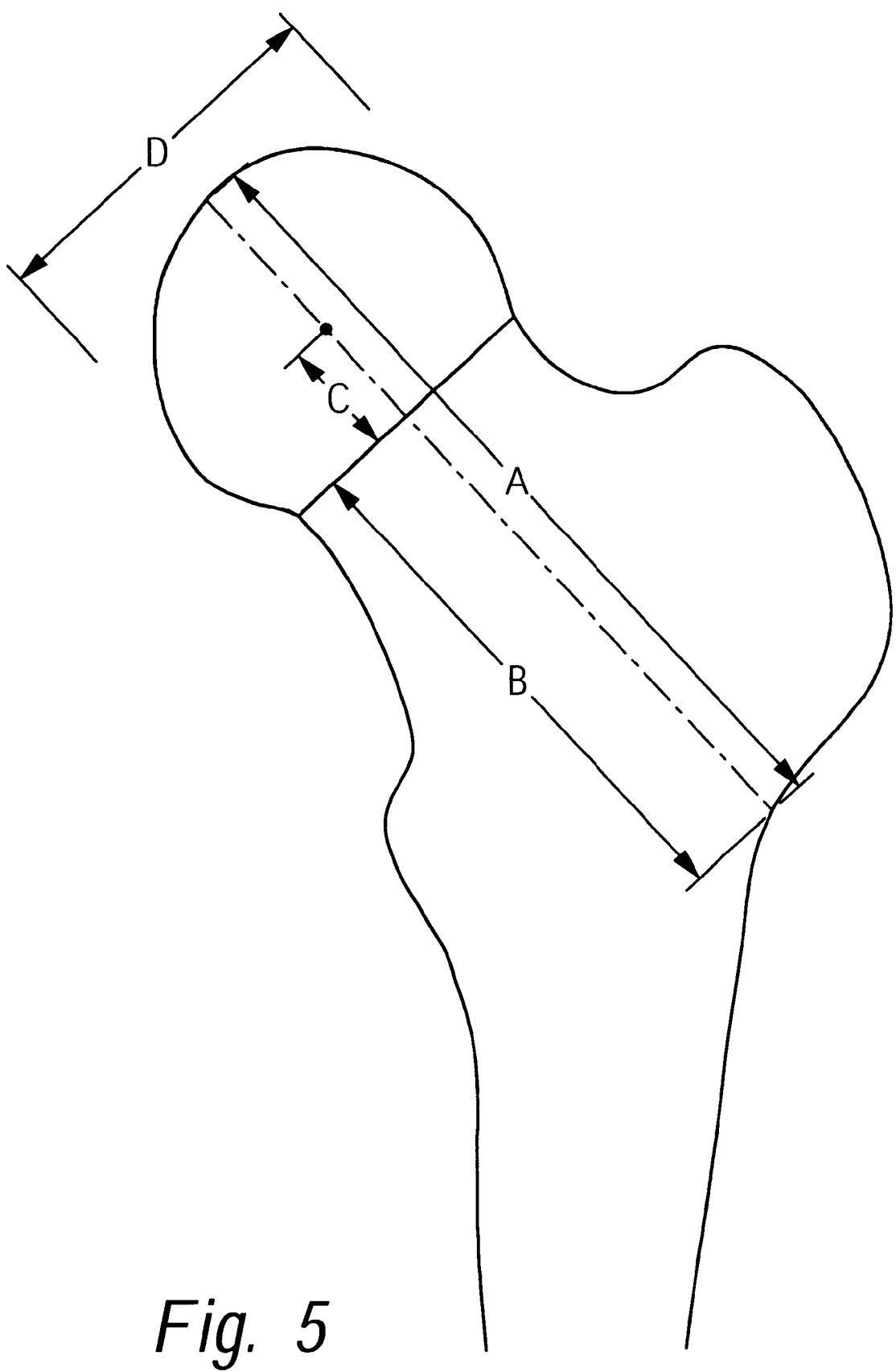
FIG. 5 depicts how the center of rotation of the femoral head can be reproduced in accordance with a preferred embodiment of the present invention.

FIG. 5 depicts how the center of rotation of the femoral head can be reproduced in accordance with a preferred embodiment of the present invention. First, distance A from the head to the lateral cortex is measured. After the femoral head is removed, distance B, from the cut surface to the lateral cortex, is measured. The diameter D of the femoral head is also measured. When these measurements are known, distance C is calculated using the formula $$C=(A-D/2)-B$$

Distance C then represents the distance from the cut surface of the femoral neck that the prosthetic femoral head center-of-rotation should be placed in order to reproduce the preoperative femoral head center-of-rotation.

Figure 6:
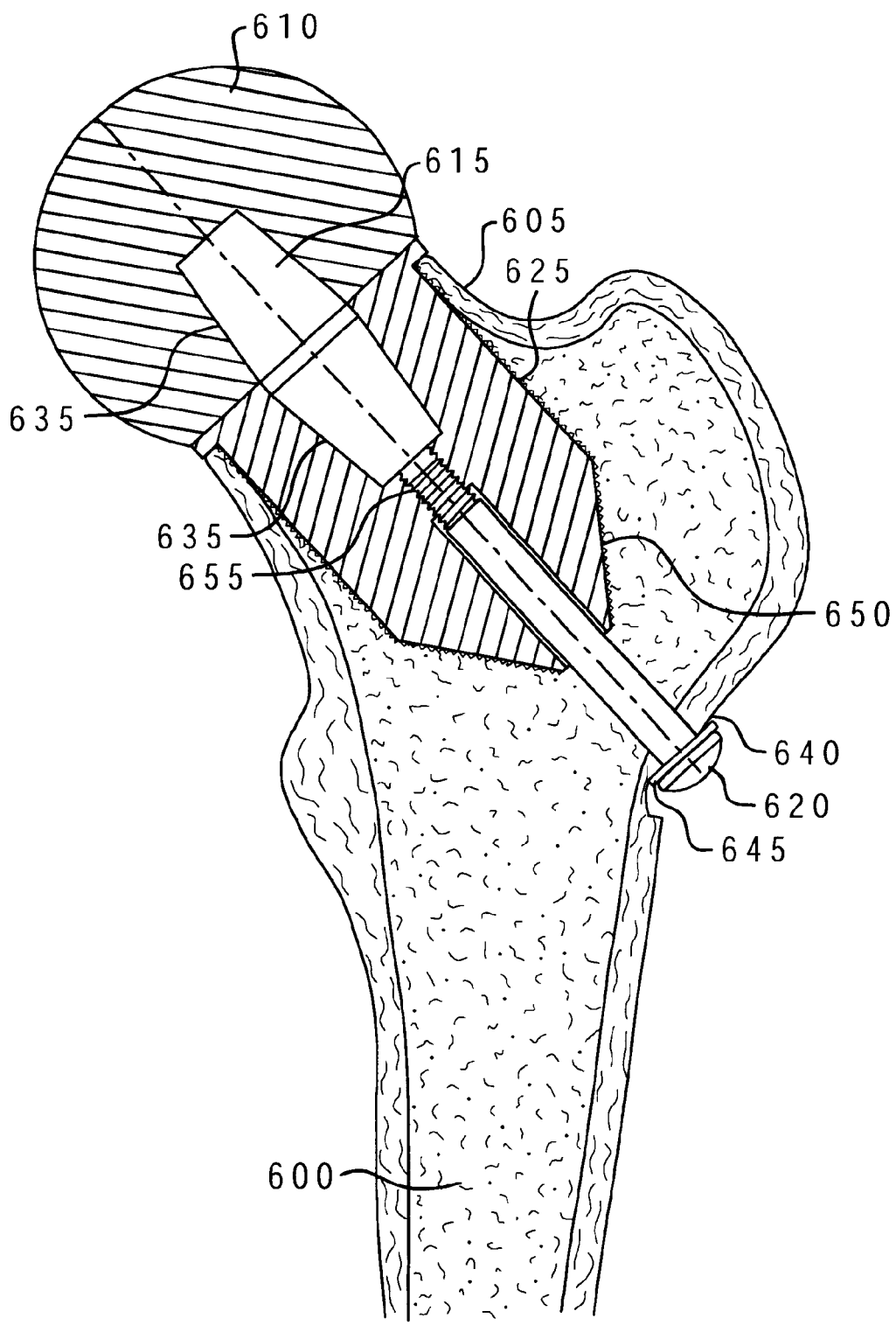
FIG. 6 depicts a prosthesis in accordance with an alternate embodiment of the present invention.

In an alternate embodiment shown in FIG. 6, compression screw 620, preferably with washer 645, is inserted through the lateral wall of the femur at location 640 and screwed into the body 625 of the femoral component. This simplifies the barrel nut portion of the design shown in FIG. 1. It would require that the screw 620 be of various lengths that would engage the body 625 of the prosthesis without reaching the depth of the hole in the femoral prosthesis. The body of the prosthesis would preferably be longer, using optional extension 650 to provide enough length so that the compression screw will be stable within the body of the prosthesis.

The remainder of FIG. 6 is similar to FIG. 1. In this figure, femur 600 is shown with femoral neck 605, joining member 615, and prosthetic head 610.

This embodiment provides an uncemented porous coated femoral prosthesis body 625 with a modular head 610 and joining member 615. The body 625 of the prosthesis include threads 655 for receiving screw 620.

Fixation to the femur will be achieved by reaming the femoral neck 605 to accommodate a cylindrical porous coated sleeve body 625, which is supported by a proximal collar and given distal stability with a compression screw 620 through the lateral wall of the femur just distal to the greater tuberosity (location 640).

After insertion, the long axis of the body of the component body 625 will coincide with the axis made in the preoperative femur 600 by an imaginary line connecting the center of the femoral neck 605 with the center of the femoral head 610. Resection of the femoral head will be measured such that the center of rotation of the femoral head 610 can be measured and reproduced as discussed with reference to FIG. 5. The femoral neck 605 will be reamed with a flat reamer that fits in the reamed canal of the femoral neck 605 to establish a flat surface. The proximal body 625 of the prosthesis will have the female end of a morse taper to allow the attachment of the femoral neck 615.

Compression screw 620 passes through the center of the body of the prosthesis. The screw 620 is preferably smooth in the segment within the body of the prosthesis and has threads on the proximal end, for engaging threads 655. The tunnel through the body of the prosthesis forms a snug fit around the smooth portion of the screw 620. Screw 620 adds stability to the construct by giving antero-posterior and varus-valgus stability to the body 625 of the prosthesis and by compressing the prosthesis on the neck 605 of the femur 600. These screws will be available in various lengths.

Male-male morse taper joining member 615 connects the body 625 of the prosthesis to the femoral head 610. Adjustments in joining member neck length will occur in this segment with several lengths of joining member segments available for each femoral body and femoral head. The joining member segment needed to exactly reproduce the center of rotation of the femoral head will be known based on the amount of bone resected.

The femoral head 610 will have a female morse taper to connect to the joining member 615. Femoral heads 610 will be of various diameters depending on the acetabulum. Ideally larger femoral head diameters (e.g., 36 mm to 60 mm) are used to both improve stability and prevent impingement of the neck on the acetabular rim. The femoral head 610 is preferably polished chrome-cobalt, as the industry standard, but other materials can be used.

Figure 7:
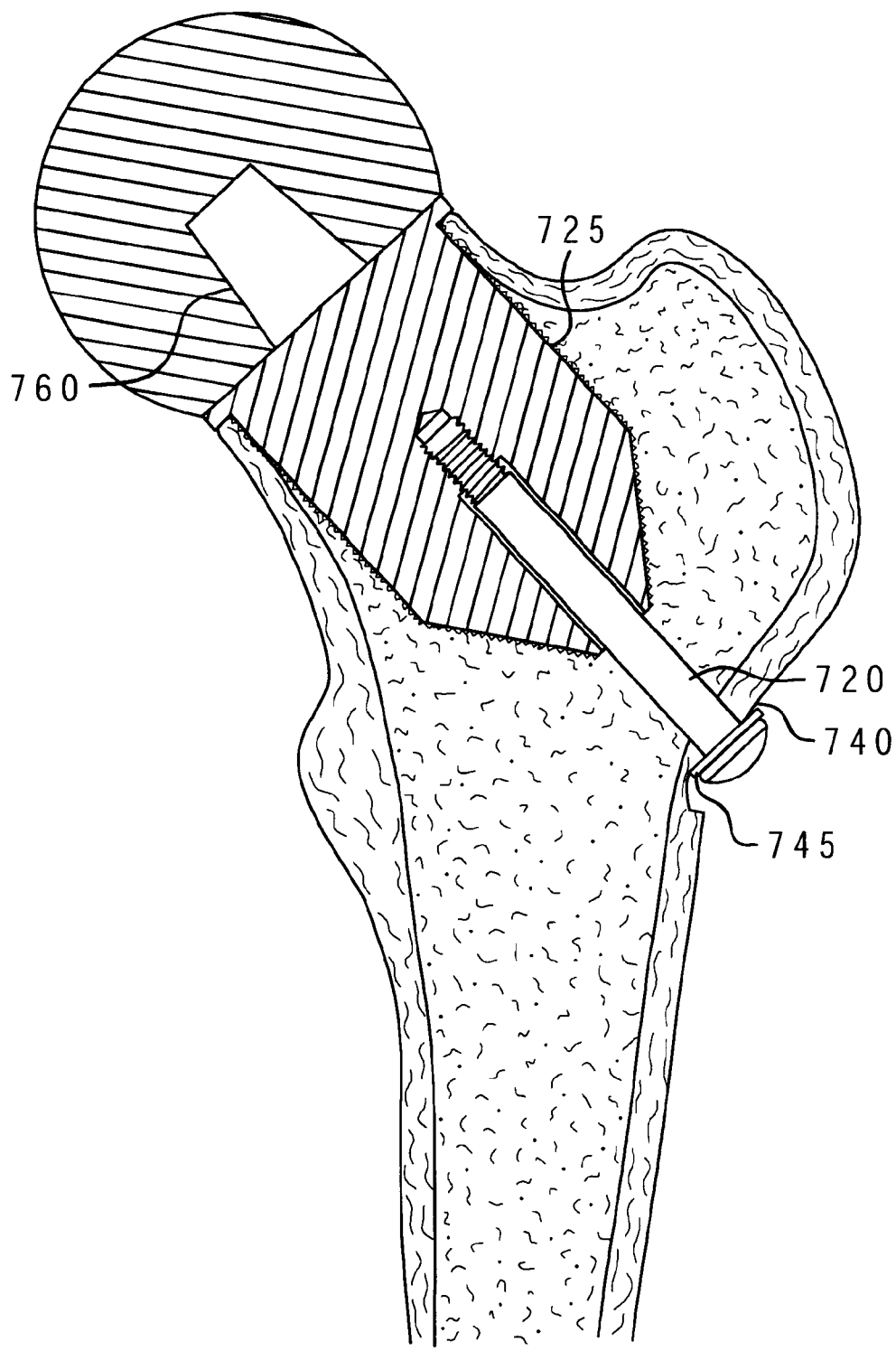
FIG. 7 depicts a prosthesis in accordance with an alternate embodiment of the present invention.

FIG. 7 shows yet another alternate embodiment of the present invention. If the compression screw 720, with washer 745, is inserted through the lateral wall of the femur at 740, the length of the body 725 of the prosthesis may not be long enough to provide adequate stability for the compression screw 720. In order to provide this stability for the compression screw, a fixed length joining member 760 on the body of the prosthesis would be necessary to act as a joining member, abandoning the modular joining member (115 in FIG. 1). The varied lengths required on the joining member would be incorporated into the femoral head either with separate individual lengths for each head diameter (2 to 3 for each diameter femoral head) or by using an interposing piece of metal to provide additional neck length. The latter is done with several femoral components available on the market today.

Modifications and Variations

As will be recognized by those skilled in the art, the innovative concepts described in the present application can be modified and varied over a tremendous range of applications, and accordingly the scope of patented subject matter is not limited by any of the specific exemplary teachings given.

While the invention has been particularly shown and described with reference to a preferred embodiment, it will be understood by those skilled in the art that various changes in form and detail may be made therein without departing from the spirit and scope of the invention.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC §112 unless the exact words "means for" are followed by a participle.

What is claimed is:

1. An implant for replacing the proximal portion of a femur having a substantially intact natural femoral neck and a lateral side opposite the femoral neck, the implant comprising:

a solid body member having a longitudinal axis, a distal end, and a proximal end, being configured for positioning, in use, in the natural femoral neck, the length of the solid body member along the longitudinal axis being greater than its width perpendicular to the longitudinal axis;

a head member having a distal end and a proximal substantially-spherical portion configured for positioning in a natural or prosthetic hip socket;

a joining member positioned between the distal end of the head member and the proximal end of the body member; and a fastener spaced distally from the joining member and insertable, in use, between the distal end of the body member and the exterior of the lateral side of the femur, substantially in line with the longitudinal axis of the solid body member; and wherein no other fasteners pass within or through the femur.

2. The implant of claim 1, wherein the solid body member has a length for positioning, in use, in the natural femoral neck without passage of the distal end through the lateral side of the femur.

3. The implant of claim 1, wherein the body member comprises a collar positioned at the proximal end of the body member and configured for abutting contact, in use, with a proximal surface of the reheated femoral neck.

4. The implant of claim 1 wherein the body member, the head member, and the joining member are integrally attached.

5. The implant of claim 1 wherein the body member and the joining member are an integral unit.

6. The implant of claim 1 wherein the joining member comprises at least one morse-tapered portion.

7. The implant of claim 1 wherein the joining member comprises a first morse-tapered portion which extends into a cavity in the head member and a second morse-tapered portion which extends into a cavity in the solid body member, both of the morse-tapered portions extending in substantial coaxial alignment relative to the longitudinal axis of the body member.

8. The implant of claim 1 wherein the body member, the head member, and the joining member are separable modular components.

9. The implant recited in claim 1 wherein the fastener comprises a barrel nut located at the exterior lateral side of the femur and a compression screw extending between the solid body member and the barrel nut.

10. The implant recited in claim 1 wherein the fastener comprises compression screw extending between the exterior lateral side of the femur and the solid body member.

11. The implant of claim 1 further comprising a first surface coating on at least a portion of the body member for promoting bone ingrowth into the coating following implantation.

12. The implant of claim 1, wherein the distal end of the solid body member is configured to connect with the fastener.

13. The implant of claim 1 further comprising a body extension member which extends from the distal end of the solid body member at least partially along the fastener, and which is in substantial coaxial alignment relative to the longitudinal axis of the body member.

14. The implant of claim 1 wherein at least a portion of the body member is triangular in cross section.

15. The implant of claim 1 wherein at least a portion of the body member is fluted in cross section.

16. The implant of claim 1 wherein at least a portion of the body member is scalloped in cross section.

17. The implant of claim 1 wherein at least a portion of the body member is substantially circular in cross section.

18. The implant of claim 1 wherein at least a portion of the body member is oval in cross section.

19. The implant of claim 1 wherein no additional support member is attached to the lateral side of the femur.

* * * * *

UNITED STATES PATENT AND TRADEMARK OFFICE
CERTIFICATE OF CORRECTION

PATENT NO.     : 6,695,883 B2
DATED          : February 24, 2004
INVENTOR(S)    : Theodore W. Crofford It is certified that error appears in the above-identified patent and that said Letters Patent is hereby corrected as shown below:

Column 8,
Line 34, change "reheated" to -- resected --.

Signed and Sealed this

Twenty-second Day of June, 2004

JON W. DUDAS
*Acting Director of the United States Patent and Trademark Office*